(12) United States Patent
Lee et al.

(10) Patent No.: US 10,827,975 B2
(45) Date of Patent: Nov. 10, 2020

(54) EXTERNAL INFORMATION PLATFORM IN CONJUNCTION WITH INTELLIGENT WEARABLE OUTFIT (71) Applicant: National Cheng Kung University, Tainan (TW)

(72) Inventors: Shuenn-Yuh Lee, Tainan (TW); Pau-Choo Chung, Tainan (TW); Jia-Hua Hong, Keelung (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 0 days.

(21) Appl. No.: 16/699,661

(22) Filed: Dec. 1, 2019

(65) Prior Publication Data
US 2020/0100729 A1 Apr. 2, 2020

Related U.S. Application Data (62) Division of application No. 15/175,342, filed on Jun. 7, 2016, now Pat. No. 10,531,830.

(30) Foreign Application Priority Data

Dec. 22, 2015 (TW) .............................. 104143125 A (51) Int. Cl.
A61B 5/00 (2006.01)
A61B 5/0205 (2006.01)
(Continued)

(52) U.S. Cl.
CPC .......... A61B 5/6805 (2013.01); A61B 5/0022 (2013.01); A61B 5/0024 (2013.01); A61B 5/0059 (2013.01); A61B 5/01 (2013.01); A61B 5/02055 (2013.01); A61B 5/0402 (2013.01); A61B 5/0488 (2013.01); A61B 5/08 (2013.01); A61B 5/1112 (2013.01); A61B 5/6807 (2013.01); A61B 5/7282 (2013.01); A61B 5/746 (2013.01); G06F 19/00 (2013.01); G16H 40/67 (2018.01); H04B 1/385 (2013.01);
(Continued)

(58) Field of Classification Search
CPC ... A61B 5/6804; A61B 5/6805; A61B 5/7282; A61B 5/0024; A61B 5/0022; A61B 5/0059; A61B 5/01; A61B 5/0402; A61B 5/0488; A61B 5/08; A61B 5/1112; A61B 5/6807; A61B 5/746; A61B 2560/0214; A61B 2560/0242; A61B 2560/0475; H04B 1/385; G01H 40/67; G06F 19/00
See application file for complete search history.

(56) References Cited

U.S. PATENT DOCUMENTS

| 2006/0199403 | A1* | 9/2006 | Tsai | H01R 12/716 439/74 |
| 2011/0087115 | A1* | 4/2011 | Sackner | A61B 5/0022 600/484 |
| 2015/0182795 | A1* | 7/2015 | Martikka | A63B 24/0062 340/870.07 |

* cited by examiner

Primary Examiner — Amanda Lauritzen Moher
Assistant Examiner — Chao Sheng
(74) Attorney, Agent, or Firm — Chun-Ming Shih; Lanway IPR Services (57) ABSTRACT An external information platform in conjunction with an intelligent wearable outfit provides various functional modules for measuring physiological signals in a modular design. An appropriate functional module (or even more than one functional module if desired) may be selected therefrom and arranged in the wearable outfit to extend and change functions of the wearable outfit, making the intelligent wearable outfit suitable for most users who can manage personal health appropriately.

4 Claims, 6 Drawing Sheets (51) Int. Cl.
*G16H 40/67* (2018.01)
*A61B 5/01* (2006.01)
*A61B 5/0402* (2006.01)
*A61B 5/0488* (2006.01)
*A61B 5/08* (2006.01)
*A61B 5/11* (2006.01)
*H04B 1/3827* (2015.01)
*A61B 5/0408* (2006.01)
*G06F 19/00* (2018.01)

(52) U.S. Cl.
CPC ........... *A61B 5/0006* (2013.01); *A61B 5/0008* (2013.01); *A61B 5/04085* (2013.01); *A61B 2560/0214* (2013.01); *A61B 2560/0242* (2013.01); *A61B 2560/0475* (2013.01)

EXTERNAL INFORMATION PLATFORM IN CONJUNCTION WITH INTELLIGENT WEARABLE OUTFIT

CROSS-REFERENCE TO RELATED APPLICATIONS

This application is a divisional application of U.S. patent application Ser. No. 15/175,342 filed on Jun. 7, 2016, the disclosure of which is incorporated herein by reference.

BACKGROUND OF THE INVENTION

Field of the Invention

The invention relates to a device for acquiring human physiological signals, and more particularly, to an intelligent wearable outfit capable of extending or changing physiological signal measuring functions, and an external information platform and a computer program product which are in conjunction with the intelligent wearable outfit.

Descriptions of the Related Art

An idea of making a portable or wearable electronic device, that is a concept of wearable device, has already been proposed for the sake of providing more convenience in human life. Such a wearable device is not considered successful yet in terms of meeting living requirements because of immature technology. Due to improvements in technology, medical care quality and network communication, development of a wearable outfit for a user to do personal health management tends to be combined with high technology and networks. However, this wearable outfit for personal health management cannot extend the functions thereof after it is made, and does not have intelligent and Internet functions thereby not suitable for every user. In other words, the functions of the existing wearable outfit are fixed and cannot be changed or extended in response to user's needs, and the existing wearable outfit cannot perform interconnected communication.

In view of the above, the problem to be solved promptly in the art is to provide a wearable outfit, which allows functions thereof to be changed and extended according to user's requirements.

SUMMARY OF THE INVENTION

In view of various problems of prior arts mentioned above, a primary object of the invention is to provide an intelligent wearable outfit and an external information platform and a computer program product which are in conjunction with the intelligent wearable outfit, wherein the intelligent wearable outfit is provided with various functional modules for a user to select a desirable one therefrom, such that functions of the intelligent wearable outfit can be expanded and changed.

Another object of the invention is to provide an intelligent wearable outfit and an external information platform and a computer program product which are in conjunction with the intelligent wearable outfit, wherein functional modules are embedded in functional parts of the intelligent wearable outfit such that the functional modules can be flexibly arranged and a desirable appearance of the intelligent wearable outfit can be achieved.

To achieve the above and other objects, an intelligent wearable outfit is provided in the invention, which includes an outfit body, a first functional part, at least one Nth functional part and a basic functional part. The outfit body includes a transducer, a set of wires and a plurality of assembly parts, wherein the assembly parts are dispersed in the outfit body and are connected to each other by the set of wires. The assembly parts are respectively mounted to one of the first functional part, the Nth functional part and the basic functional part in a detachable manner. The first functional part has a first expandable functional module, wherein the first expandable functional module includes a first functional chip and a first repeater. The Nth functional part has an Nth expandable functional module, wherein the Nth expandable functional module includes an Nth functional chip and an Nth repeater, wherein N is an integral equal to or larger than two. The basic functional part has a basic functional module, wherein the basic functional module includes a basic repeater, a power supply, a basic functional chip and a wireless transceiver. The basic, first and Nth repeaters are electrically connected to each other by the set of wires, so as to allow electrical connection between the basic, first and Nth functional chips, allow the power supply to provide power for operation of the first and Nth functional chips, and allow the transducer to measure physiological signals. The physiological signals measured by the transducer are transferred to the basic functional chip and sent out by the wireless transceiver.

Preferably, the first or Nth functional chip is selected from the group consisting of physiological signal sensor chip, microphone control chip, speaker control chip, global positioning system chip, camera control chip, temperature sensor chip, inertia sensor chip, environment sensor chip and memory chip. The first and Nth expandable functional modules are connected to each other by the set of wires to form a group for functional expansion of the basic functional module and form an interconnected communication network configuration.

Preferably, the first, Nth and basic functional parts respectively have a carrier and a lid. The carriers of the functional parts are for carrying the first and Nth expandable functional modules and the basic functional module respectively. The lids of the functional parts cover the corresponding carriers for protecting the functional modules carried by the carriers. The set of wires pass through the carriers and are electrically connected to the functional modules carried by the carriers. The carriers further have assembly structures respectively for being mounted to the assembly parts. The lids are formed with exposed features and are provided with switch, indicator, camera, antenna, speaker and/or microphone, which is electrically connected to the functional modules carried by the carriers.

The invention further provides an external information platform in conjunction with the intelligent wearable outfit. The external information platform includes a control module and a wireless transceiving module. The control module is for controlling the wireless transceiving module to allow the wireless transceiving module to communicate with the wearable outfit. The wireless transceiving module is for receiving the physiological signals sent from the wireless transceiver or for feeding back control signals to the first and Nth expandable functional modules and the basic functional module.

Preferably, the external information platform further includes a storage module, a processing module and an abnormality indicating module. The storage module is for storing the physiological signals received by the wireless transceiving module and storing the control signals being fed back to the first and Nth expandable functional modules and the basic functional module. The processing module is for analyzing the physiological signals received by the wireless transceiving module to see if the physiological signals are abnormal, and/or for retrieving and classifying characteristics of the physiological signals. The abnormality indicating module is for sending out an abnormality indication if the physiological signals are analyzed to be abnormal by the processing module.

Preferably, the wireless transceiving module is further for receiving operating statuses of the first and Nth expandable functional modules and/or the basic functional module. The processing module is further for analyzing if the first and Nth expandable functional modules and/or the basic functional module operate abnormally according to the operating statuses received by the wireless transceiving module. The control module is further for controlling operation of the first and Nth expandable functional modules and/or the basic functional module to form an interconnected communication network configuration.

The invention further provides a computer program product with a built-in control program, wherein when the computer program product loads and executes the control program, operation of the above external information platform is completed.

The invention further provides an intelligent wearable outfit including: an outfit body including a transducer and a set of wires; a first expandable functional module; at least one Nth expandable functional module, wherein N is an integral equal to or larger than two; and a basic functional module. The first and Nth expandable functional modules and the basic functional module are detachably mounted to the outfit body. The first and Nth expandable functional modules are electrically connected to each other by the set of wires to form an expandable functional module group, allowing the transducer to measure physiological signals. The expandable functional module group is further electrically connected to the basic functional module by the set of wires so as to allow the basic functional module, first expandable functional module and Nth expandable functional module to be electrically interconnected to form an interconnected communication network configuration, such that the physiological signals measured by the transducer can be transferred to the basic functional module by the set of wires.

In comparison to prior arts, the intelligent wearable outfit of the invention provides various functional modules which can be selectively and flexibly arranged and are formed with a miniaturization configuration. The functional modules are respectively embedded in corresponding functional parts. Appropriate functional parts may be selected therefrom for use in the outfit body according to user's needs to extend functions of the intelligent wearable outfit, making the intelligent wearable outfit of the invention suitable for most users.

BRIEF DESCRIPTION OF THE DRAWINGS

The above and other aspects, features and other advantages of the present invention will be more clearly understood from the following detailed description taken in conjunction with the accompanying drawings, in which:

FIG. 6-1 is a structure diagram showing the functional part of the invention.

FIG. 6-2 is another structure diagram showing the functional part of the invention.

DETAILED DESCRIPTION OF THE PREFERRED EMBODIMENT

Embodiments of the present invention will now be described in detail with reference to the accompanying drawings. The invention may, however, be embodied in many different forms and should not be construed as being limited to the embodiments set forth herein. Rather, these embodiments are provided so that this disclosure will be thorough and complete, and will fully convey the scope of the invention to those skilled in the art. In the drawings, the shapes and dimensions of elements may be exaggerated for clarity, and the same reference numerals will be used throughout to designate the same or like components.

The invention provides an intelligent wearable outfit, which comprises various expandable functional modules for measuring physiological signals. A user may desirably select at least one of the expandable functional modules to be in use with the intelligent wearable outfit. This allows the intelligent wearable outfit to change and extend its functions according to user's needs. The intelligent wearable outfit can be a portable accessory such as shoe, bag, belt and/or scarf, or clothes such as skirt and/or shirt (with or without sleeves), or any kind of clothing. This wearable outfit has a flexible form and appearance for the user to choose to fit his/her living according to different occasions and weather. It should be understood that, the intelligent wearable outfit of the invention is illustrated below, but not limited to, an embodiment of a shirt.

The embodiments of the invention are described with reference to FIGS. 1 to 6.

Figure 1:
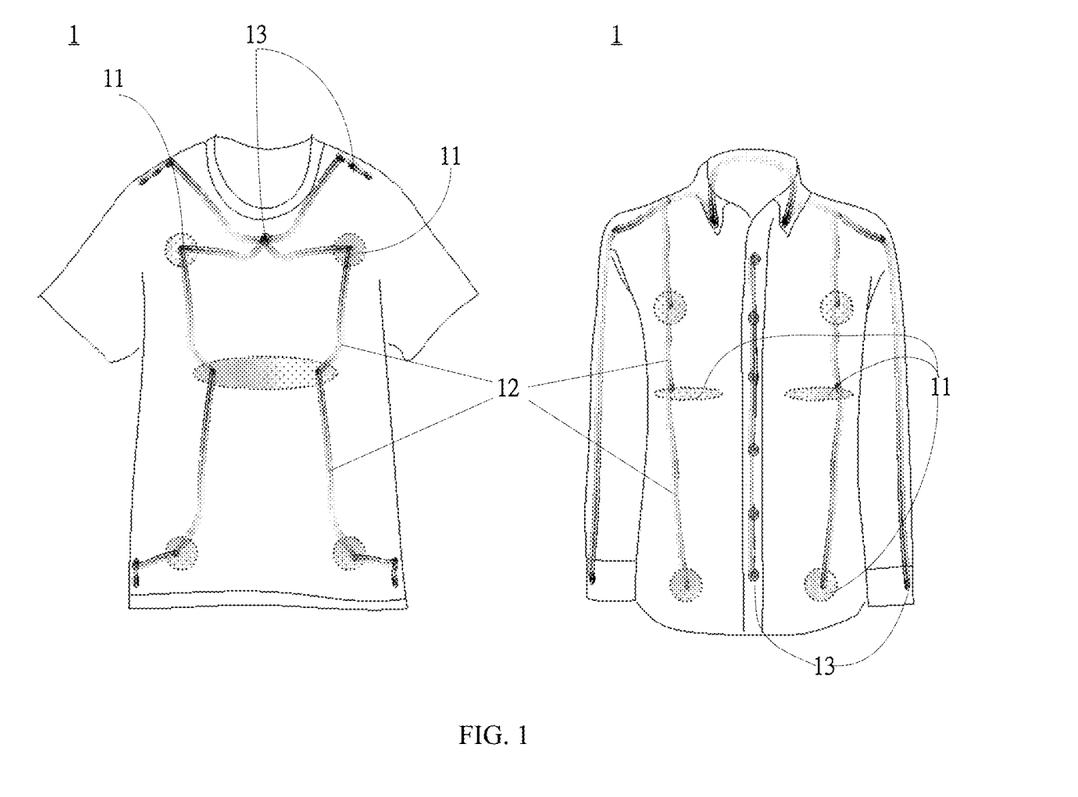
FIG. 1 is a schematic view showing an embodiment of an intelligent wearable outfit of the invention.

In the embodiment of FIG. 1, the intelligent wearable outfit is formed with a plurality of assembly parts, which are dispersed (or disposed in different positions) and exposed. The assembly parts may be connected to various functional parts having functional modules, such that physiological signal sensing and health management functions provided by the intelligent wearable outfit can be extended and changed. The assembly parts may also be connected to an accessory to desirably modify the appearance of the intelligent wearable outfit according to user's requirements.

As shown in FIG. 1, the intelligent wearable outfit of the invention includes an outfit body 1 having a transducer 11, a set of wires 12, and a plurality of assembly parts 13, wherein the assembly parts 13 are separately disposed. The transducer 11 and the wires 12 may be mounted by sewing in the outfit body 1. The transducer 11 is used to measure physiological signals in a human body. The transducer uses a recognizing element to sense physiological signals from a living sample, and can be, but is not limited to, an electrode. The transducer can be a sensor, which obtains physiological signals in relation to energy conversion of such as light, electricity, dynamics, magnetism, heat, fluidity, inertia or sound. The physiological signals include, but are not limited to, electrocardiography (ECG) signals, electromyography (EMG) signals, temperature sensing signals, humidity sensing signals, breath sensing signals and inertia sensing signals. In the invention, the design of the transducer 11 may be modified according to the physiological signals to be measured. The number and position of the transducer 11 are also flexible in the outfit body 1. The wires 12 can be fiber wires covered with water resistant material, such that the intelligent wearable outfit is washable for the sake of hygiene.

The intelligent wearable outfit of the invention further includes a plurality of functional parts detachably mounted to at least one of the assembly parts 13. Particularly, the functional parts may be attached to the assembly parts 13 and may also be detached therefrom. The intelligent wearable outfit further includes at least a basic functional module and at least an expandable functional module, which are disposed or embedded in the functional parts. More description thereof is as follows.

Figure 2:
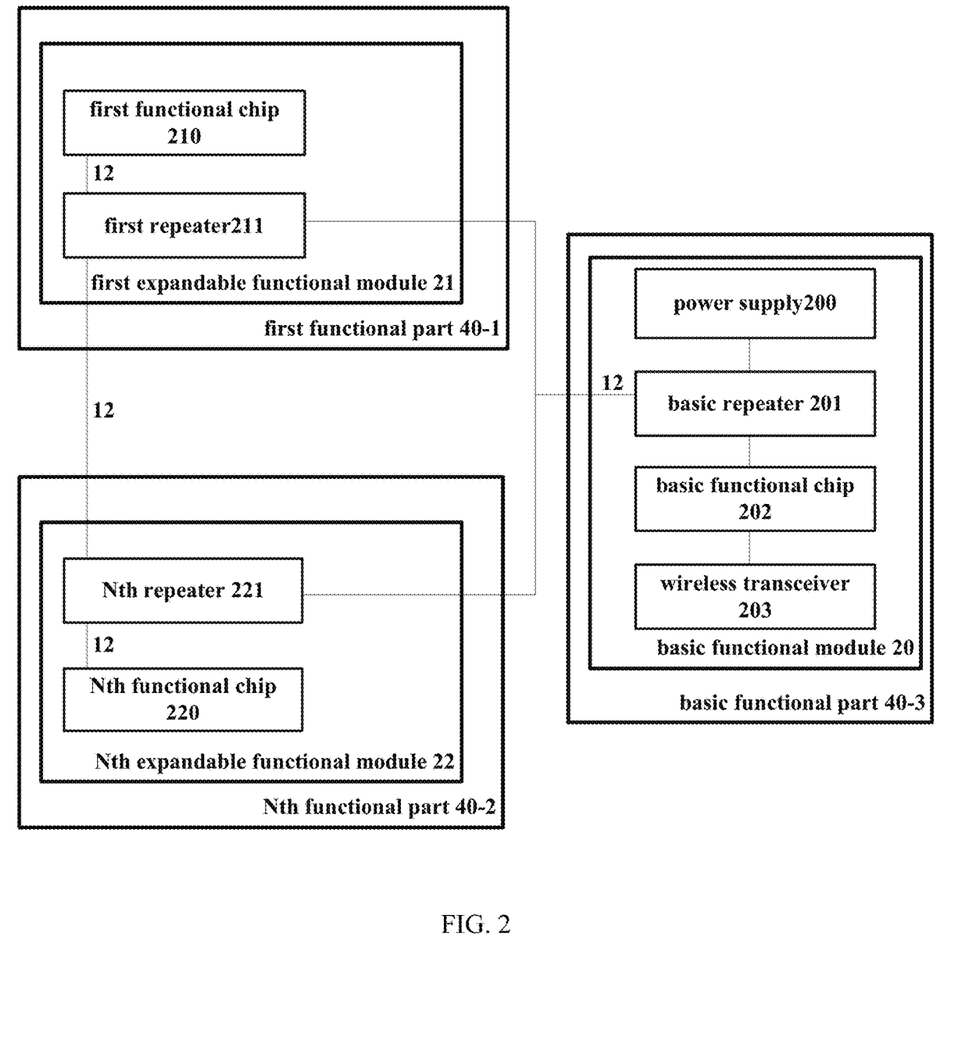
FIG. 2 is a schematic view showing the relationship between various functional modules of the intelligent wearable outfit of the invention.

FIG. 2 schematically shows the relationship between a basic functional module and expandable functional modules. It should be understood that, FIG. 2 merely illustrates one type connection between the basic functional module and the expandable functional modules. The invention may also be implemented by increasing input/output ports of repeaters to connect the basic functional module and the expandable functional modules in a tree network manner to form a functional group.

As shown in FIG. 2, the intelligent wearable outfit of the invention includes a first functional part 40-1, an Nth functional part 40-2, and a basic functional part 40-3, wherein N is an integral equal to or larger than two. The first, Nth and basic functional parts 40-1, 40-2, 40-3 are correspondingly provided with a first expandable functional module 21, an Nth expandable functional module 22 and a basic functional module 20. The basic functional module 20 includes a power supply 200, a basic repeater 201, a basic functional chip 202 and a wireless transceiver 203. The first expandable functional module 21 includes a first functional chip 210 and a first repeater 211. The Nth expandable functional module 22 includes an Nth functional chip 220 and an Nth repeater 221. In FIG. 2, the basic functional module 20, the first expandable functional module 21 and the Nth expandable functional module 22 have the respective basic, first and Nth repeaters 201, 211, 221 thereof electrically interconnected by the set of wires 12, such that the basic, first and Nth functional chips 202, 210, 220 can be electrically coupled to each other. This allows the first and Nth expandable functional modules 21, 22 to form an expandable functional group, which serves as a functional extension for the basic functional module 20, and achieves Internet communication between the functional modules, particularly Internet of things (IOT) communication. More specifically, the functional modules 20, 21, 22 may communicate with each other by means of an interconnected communication network configuration so as to allow various functional modules to share information.

Moreover, the power supply 200 may supply power to the first and Nth expandable functional modules 21, 22 by means of the set of wires 12 through the basic, first and Nth repeaters 201, 211, 221, in order to make the first and Nth expandable functional modules 21, 22 operate properly. Therefore, the transducer 11 of the intelligent wearable outfit may measure physiological signals, and the measured physiological signals can be transferred to the basic functional chip 202 by the set of wires 12, for further processing. The basic functional chip 202 may send the physiological signals out through the wireless transceiver 203, or receive control signals from an external information platform so as to control the first and Nth expandable functional modules 21, 22 and provide the IOT function. The first and Nth functional chips 210, 220 are respectively selected from a group consisting of physiological signal sensor chip, microphone control chip, speaker control chip, global positioning system (GPS) chip, camera control chip, temperature sensor chip, inertia sensor chip, environment sensor chip and memory chip.

Figure 3:
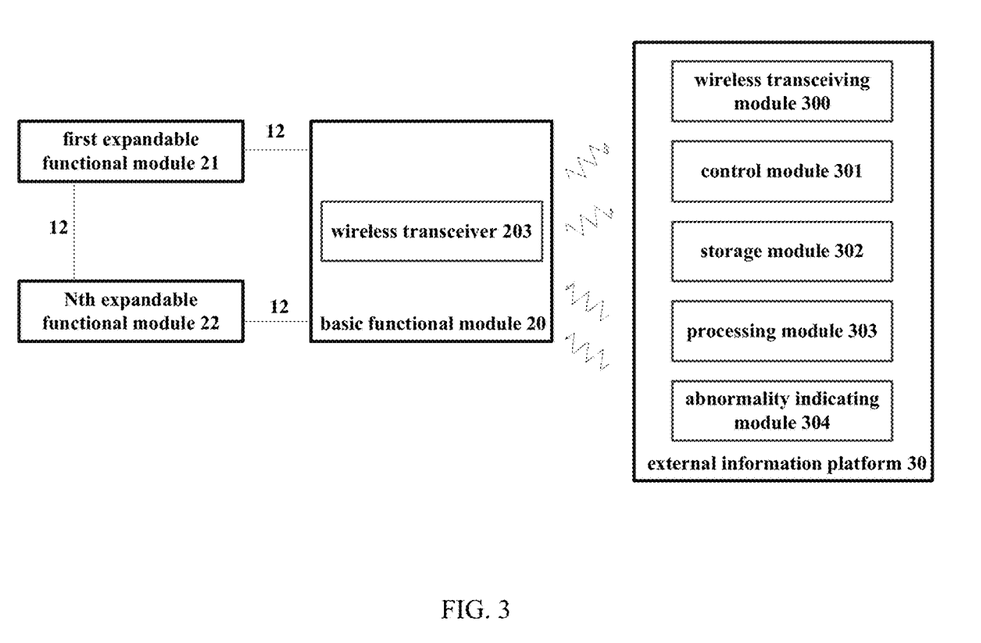
FIG. 3 is a schematic view showing the relationship between various functional modules of the intelligent wearable outfit of the invention and an external information platform.

As shown in FIG. 3, the above basic functional chip 202 sends the physiological signals out to an external information platform 30 via the wireless transceiver 203. The external information platform 30 may be provided in a computer program product with a built-in control program. The computer program product can be, for example, smart phone, personal computer or personal digital assistant device. When the computer program product loads and executes the control program, it may retrieve the information received by all the functional modules of the intelligent wearable outfit, and may alternatively control all the functional modules and provide IOT information thereto. Moreover, the external information platform 30 may process (such as analyze, record, etc.) the retrieved information, so as to perform personal heath management for the user.

Particularly, the external information platform 30 includes a wireless transceiving module 300, a control module 301, a storage module 302, a processing module 303 and an abnormality indicating module 304. The control module 301 controls the wireless transceiving module 300 in a manner that the wireless transceiving module 300 may communicate with the intelligent wearable outfit and receive the physiological signals sent from the wireless transceiver 203 or feed back control signals via the wireless transceiver 203 to the first and Nth expandable functional modules 21, 22 and the basic functional module 20. The storage module 302 may store the physiological signals received by the wireless transceiving module 300 and the control signals being fed back to the first and Nth expandable functional modules 21, 22 and the basic functional module 20. The processing module 303 may retrieve and classify characteristics of the physiological signals, and may analyze the physiological signals received by the wireless transceiving module 300 to see if the signals are abnormal. When the physiological signals are analyzed to be abnormal, the processing module 303 allows the abnormality indicating module 304 to send out an abnormality indication. The processing module 303 may also transfer the analyzed results of the physiological signals to the cloud and/or a medical institute through a communication device such as smart phone, personal computer or personal digital assistant device.

Moreover, the wireless transceiving module 300 of the external information platform 30 may receive operating statuses of the basic functional module 20 and the first and Nth expandable functional modules 21, 22. Besides retrieving and classifying characteristics of the physiological signals, the processing module 303 may also analyze if the basic functional module 20 and the first and Nth expandable functional modules 21, 22 operate abnormally, and allow the abnormality indicating module 304 to send out an abnormality indication when the functional modules 20, 21, 22 are analyzed to be operating abnormally.

It should be noted, various functional modules of the invention (the basic functional module and the first and Nth expandable functional modules) of the invention are formed with a miniaturization configuration in the functional parts. The functional parts have flexible structures and the corresponding modules are not limited to those certain functions. Generally, a single functional part is for implementing a single function (expandable function or basic function). Alternatively, a plurality of functional modules can be integrated in a chip and thus one functional part may perform multiple functions.

Figure 4:
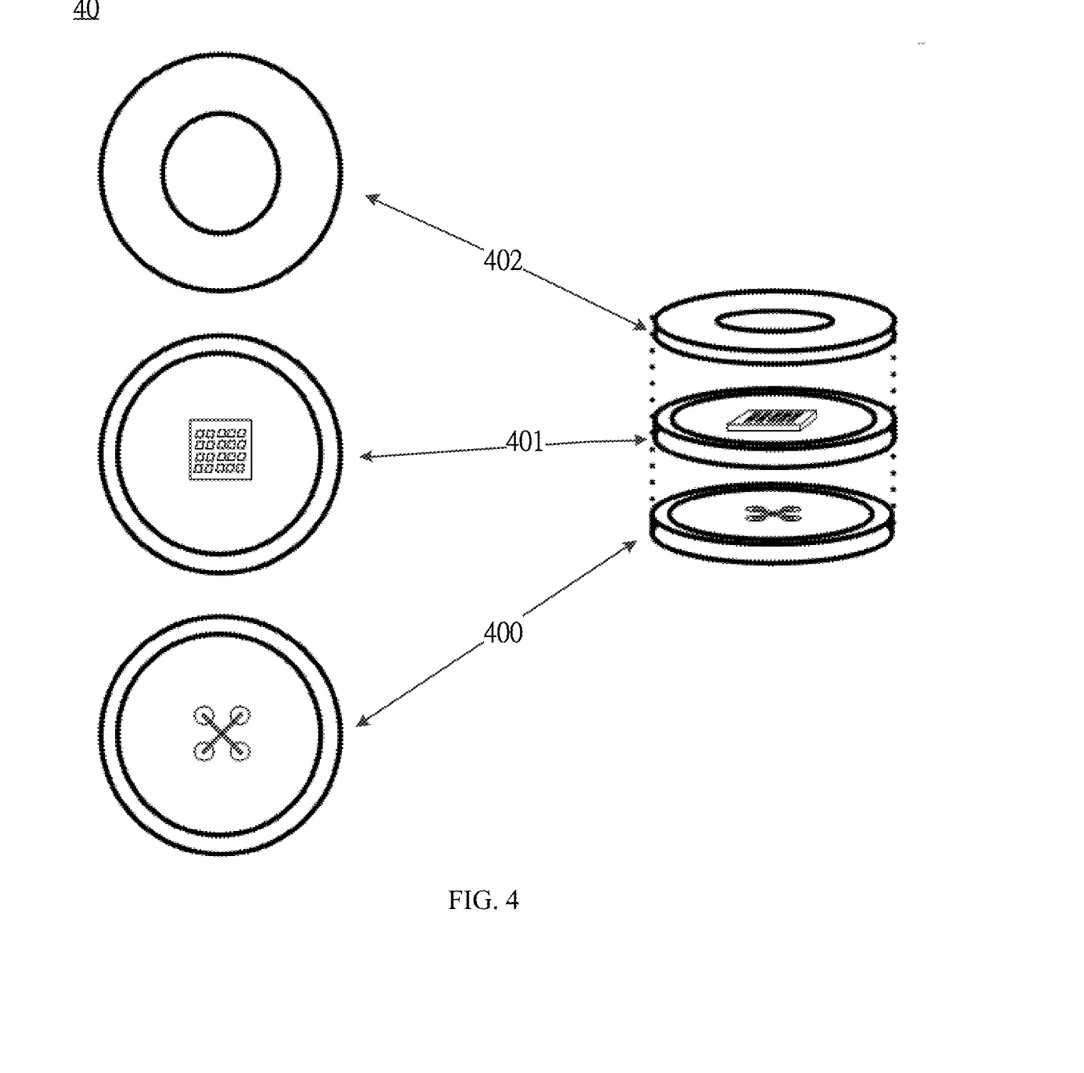
FIG. 4 is a structure diagram showing a functional part according to an embodiment of the intelligent wearable outfit of the invention.

Structure of the functional part of the invention is described as follows with reference to FIG. 4. As shown in FIG. 4, the functional part 40 may be formed as a button. It includes a carrier 400, a functional module 401 and a lid 402. The carrier 400 is used to carry the functional module 401. The set of wires disposed on the intelligent wearable outfit pass through the carrier 400 and are electrically connected to the functional module 401. The carrier 400 is further provided with an assembly structure and can be detachably mounted to the assembly part of the intelligent wearable outfit. This makes the functional part 40 more flexibly attached to the intelligent wearable outfit, thereby allowing the intelligent wearable outfit to have functional expansion or modification desirably. The lid 402 covers the carrier 400 to protect the functional module 401 carried on the carrier 400. The functional module 401 is the basic functional module or expandable functional module described above.

Figure 5:
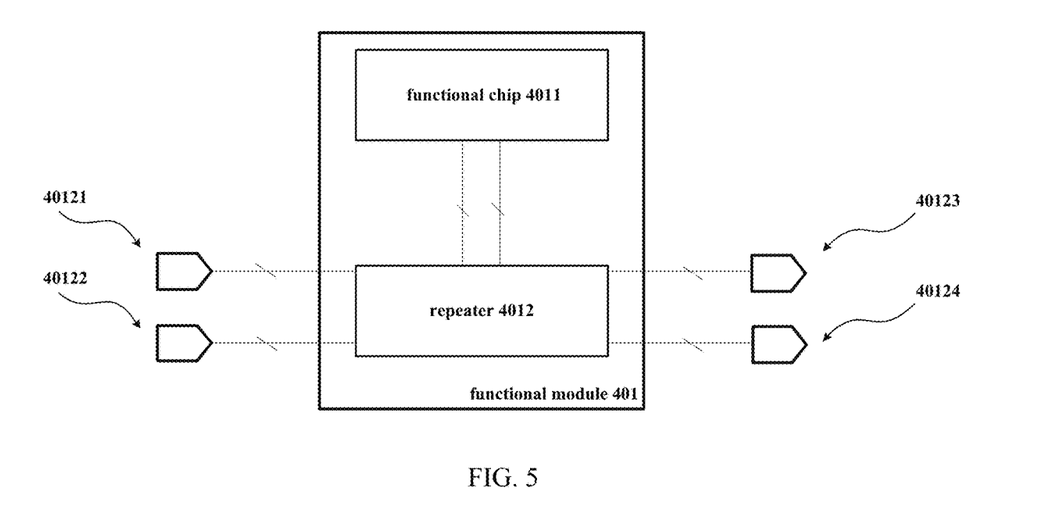
FIG. 5 is a configuration diagram showing an expandable functional module of the invention.

FIG. 5 is a configuration diagram of the above functional module 401. The functional module 401 primarily includes two portions: a functional chip 4011 and a repeater 4012. The functional chip 4011 is a chip for providing basic control functions and various application functions, and may also be a sensor chip. For example, it can be physiological signal sensor chip, microphone control chip, speaker control chip, GPS chip, camera control chip, temperature sensor chip, inertia sensor chip, memory chip, IOT control chip, power supply chip, wireless transceiver chip, or integration chip integrated with multiple functions described above. The repeater 4012 is connected to the functional chip 4011, for transmitting electricity, control signals and information. Particularly, the repeater 4012 may transmit electricity, control signals and information required for the operation of the functional chip 4011. As shown in FIG. 5, the repeater 4012 inputs and/or outputs the electricity, control signals and information via input/output ports 40121, 40122, 40123, 40124 thereof. The repeater 4012 may be coupled to other chip modules so as to expand and transmit Internet information and establish an interconnected communication network configuration. The repeater 4012 has a flexible number of the input/output ports, which may be increased or decreased according to Internet or functional requirements.

Figure 61:
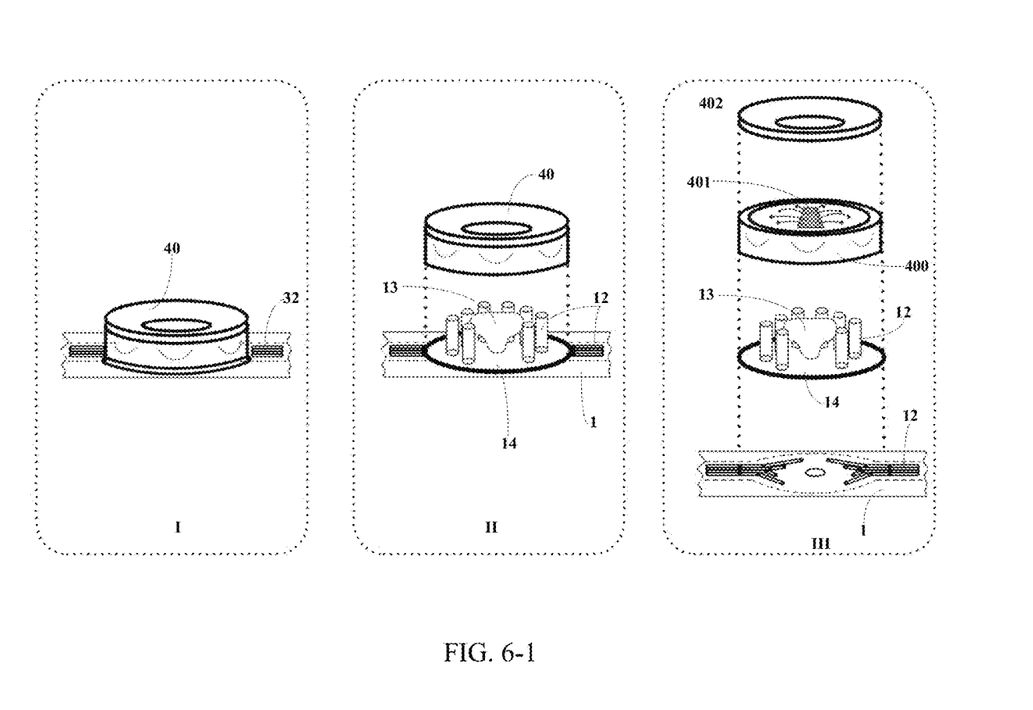
Figure 62:
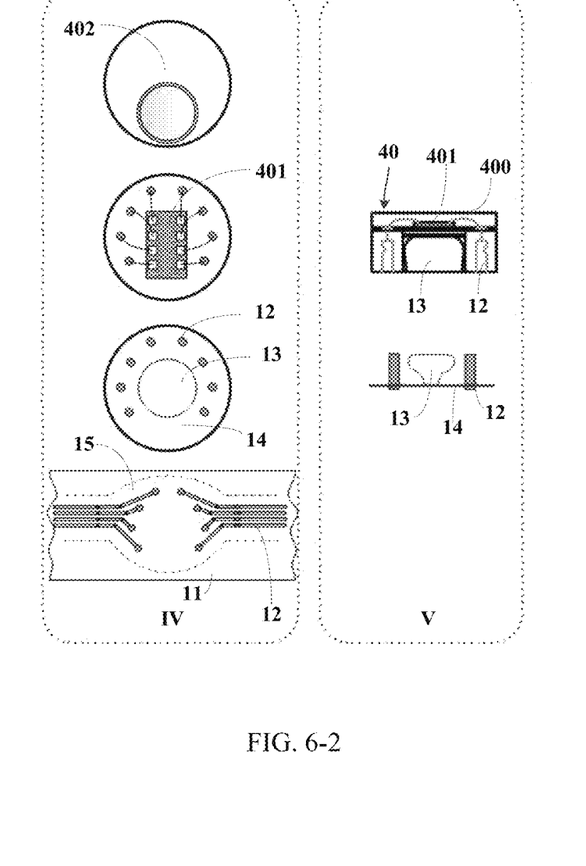

FIG. 6-1 and FIG. 6-2 are structure diagrams of the functional part of the invention. Area I of FIG. 6-1 shows a state of the functional part 40 being attached to the outfit body 1. Area II of FIG. 6-1 shows a state of the functional part 40 being detached from the outfit body 1, wherein the outfit body 1 is provided with the assembly part 13 thereon for attaching the functional part 40, and a mounting plate 14 for mounting the assembly part 13 to the outfit body 1. Preferably, the assembly part 13 is made of an elastic material and can be flexibly shaped, so as to allow easy attachment and detachment between the functional part 40 and the assembly part 13. This means that the functional part 40 is detachably mounted to the assembly part 13.

Area III of FIG. 6-1 shows that, the set of wires 12 extend through the mounting plate 14 towards the functional part 40 and also through the carrier 400 to be electrically connected to the functional module 401, so as to transmit electricity, control signals, information and Internet information required for the functional module 401. The functional module 401 can be electrically coupled to the set of wires 12 by using guy wires, conductive wires, conductive cotton, circuit or any electrical connection material or by using any electrical connection means. The mounting plate 14 can be fixed to the outfit body 1 by adhering or sewing.

Area IV and Area V of FIG. 6-2 show a breakdown state of the functional part 40. As shown, the lid 402 may be formed with an exposed feature, and for use in the operation of the functional module 401, may further be provided with switch, indicator, camera, antenna, speaker and/or microphone. The outfit body 1 is also provided with a cover layer 15 thereon for covering and protecting the wires 12 to keep the wires 12 intact in conductivity.

Therefore, in the intelligent wearable outfit and the external information platform in conjunction therewith as proposed in the invention, various functional modules are provided in corresponding functional parts, and a user may flexibly select a desirable functional part for use with the intelligent wearable outfit. The intelligent wearable outfit of the invention allows functional expansion and modification to be achieved by different arrangements of functional parts. The intelligent wearable outfit of the invention thereby has flexibly adjusted and integrated functions.

The examples above are only illustrative to explain principles and effects of the invention, but not to limit the invention. It will be apparent to those skilled in the art that modifications and variations can be made without departing from the scope of the invention. Therefore, the protection range of the rights of the invention should be as defined by the appended claims.

What is claimed is:

1. An external information platform in conjunction with an intelligent wearable outfit, the intelligent wearable outfit including an outfit body including an irremovable transducer, a set of wires, a plurality of assembly parts, and a plurality of mounting plates for mounting the plurality of assembly parts to the outfit body, wherein the assembly parts and the transducer are dispersed in the outfit body and are connected to each other by the set of wires; a plurality of first functional parts, each of the first functional parts having a first expandable functional module, wherein the first expandable functional module includes a first functional chip and a first repeater, wherein the plurality of first functional parts are formed as buttons, and at least one of the plurality of first functional parts are detachably assembled to at least one of the assembly parts; a plurality of Nth functional parts, each of the Nth functional parts having an Nth expandable functional module, wherein the Nth expandable functional module includes an Nth functional chip and an Nth repeater, wherein N is an integral equal to or larger than two, wherein the plurality of Nth functional parts are formed as buttons, and at least one of the plurality of Nth functional parts are detachably assembled to at least one of the assembly parts; and a basic functional part formed as a button and having a basic functional module, wherein the basic functional module includes a basic repeater, a power supply, a basic functional chip and a wireless transceiver, wherein the basic functional part is detachably assembled to one of the assembly parts except those assembly parts assembled to the at least one first functional part and the at least one Nth functional part; wherein the set of wires extend through the plurality of mounting plates towards the first functional part, the at least one Nth functional part, and the basic functional part, and the set of wires are disposed around the assembly parts; wherein each of the first functional part, the at least one Nth functional part, and the basic functional part is attached to the outfit body by the corresponding assembly part; wherein each of the assembly parts is made of an elastic material and is able to be flexibly shaped, so as to allow easy attachment and detachment between the first functional part, the at least one Nth functional part, the basic functional part and the corresponding assembly part, and wherein the basic, first and Nth repeaters are electrically connected to each other by the set of wires, so as to allow electrical connection between the basic, first and Nth functional chips, allow the power supply to provide power from the basic repeater to the first repeater of the first functional part and the Nth repeater of the Nth functional part for operation of operating the first and Nth functional chips, and allow the first functional chip and the Nth functional chip to respectively control the transducer to measure physiological signals; wherein the physiological signals measured by the transducer are transferred to the basic functional chip and sent out by the wireless transceiver; wherein an amount of the assembly parts is larger than total amount of the first functional parts and the Nth functional parts, such that users are able to add or remove different types and quantities of the first functional part and the Nth repeater of the Nth functional part according the users' need, the external information platform including:

a control module and a wireless transceiving module, wherein the control module is for controlling the wireless transceiving module to allow the wireless transceiving module to communicate with the intelligent wearable outfit, wherein the wireless transceiving module is for receiving the physiological signals sent from the wireless transceiver or for feeding back control signals to the first and Nth expandable functional modules and the basic functional module.

2. The external information platform according to claim 1, further including:

a storage module for storing the physiological signals received by the wireless transceiving module and storing the control signals being fed back to the first and Nth expandable functional modules and the basic functional module;

a processing module for analyzing the physiological signals received by the wireless transceiving module to see if the physiological signals are abnormal, or for retrieving and classifying characteristics of the physiological signals; and an abnormality indicating module for sending out an abnormality indication if the physiological signals are analyzed to be abnormal by the processing module.

3. The external information platform according to claim 2, wherein the wireless transceiving module is further for receiving operating statuses of the first and Nth expandable functional modules or the basic functional module; and the processing module is further for analyzing if the first and Nth expandable functional modules or the basic functional module operate abnormally according to the operating statuses received by the wireless transceiving module.

4. The external information platform according to claim 1, wherein the control module is further for controlling operation of the first and Nth expandable functional modules or the basic functional module to form an interconnected communication network configuration.

\* \* \* \* \*